United States Patent
Buessing et al.

(10) Patent No.: US 9,468,756 B2
(45) Date of Patent: Oct. 18, 2016

(54) ELECTRODE DEVICE FOR A MEDICAL IMPLANT, AND A MEDICAL IMPLANT COMPRISING AN ELECTRODE DEVICE

(71) Applicant: BIOTRONIK SE & Co. KG, Berlin (DE)

(72) Inventors: Heinrich Buessing, Berlin (DE); Jens Rump, Berlin (DE)

(73) Assignee: BIOTRONIK SE & CO. KG, Berlin (DE)

( * ) Notice: Subject to any disclaimer, the term of this patent is extended or adjusted under 35 U.S.C. 154(b) by 0 days.

(21) Appl. No.: 14/468,247

(22) Filed: Aug. 25, 2014

(65) Prior Publication Data

US 2015/0080997 A1 Mar. 19, 2015

Related U.S. Application Data

(60) Provisional application No. 61/878,060, filed on Sep. 16, 2013.

(51) Int. Cl.
*A61N 1/08* (2006.01)
*A61N 1/05* (2006.01)

(52) U.S. Cl.
CPC . *A61N 1/08* (2013.01); *A61N 1/05* (2013.01); *A61N 1/056* (2013.01); *A61N 1/0563* (2013.01); *A61N 2001/086* (2013.01)

(58) Field of Classification Search
CPC .......... A61N 1/375; A61N 1/05; A61B 1/055
USPC ............................... 607/36, 63, 116; 600/410
See application file for complete search history.

(56) References Cited

U.S. PATENT DOCUMENTS

| | | | |
|---|---|---|---|
| 2006/0085043 A1* | 4/2006 | Stevenson | A61N 1/3754 607/36 |
| 2008/0039709 A1* | 2/2008 | Karmarkar | 600/410 |
| 2008/0116997 A1 | 5/2008 | Dabney | |
| 2009/0040131 A1 | 2/2009 | Mosallaei | |
| 2009/0171421 A1* | 7/2009 | Atalar et al. | 607/63 |
| 2011/0230943 A1* | 9/2011 | Johnson | A61N 1/05 607/116 |
| 2012/0296350 A1 | 11/2012 | Kar | |

FOREIGN PATENT DOCUMENTS

CN 102826842 A 12/2012

OTHER PUBLICATIONS

European Search Report received from EP Application Serial No. 14180608, dated Jan. 22, 2015, 5 pages.
David Souriou, "Antenna miniaturization and Nanoferrite Magneto-Dielectric Materials", 14$^{th}$ International Symposium on Antenna Technology and Applied Electromagnetics and the American Electromagnetics Conference; (2010), 1-4. France.

* cited by examiner

*Primary Examiner* — Carl H Layno
*Assistant Examiner* — Jon Eric C Morales
(74) *Attorney, Agent, or Firm* — Arc IP Law, PC; Joseph J. Mayo

(57) ABSTRACT

A medical implant and an electrode device for a medical implant, wherein the electrode device includes a distal end, a proximal end, and an electric transmission line that extends between the distal end and the proximal end. The transmission line includes at least one adaptive element. The at least one adaptive element includes a magnetodielectric material, which, under the action of a magnetic field, changes one or more of its electric and magnetic properties.

16 Claims, 2 Drawing Sheets

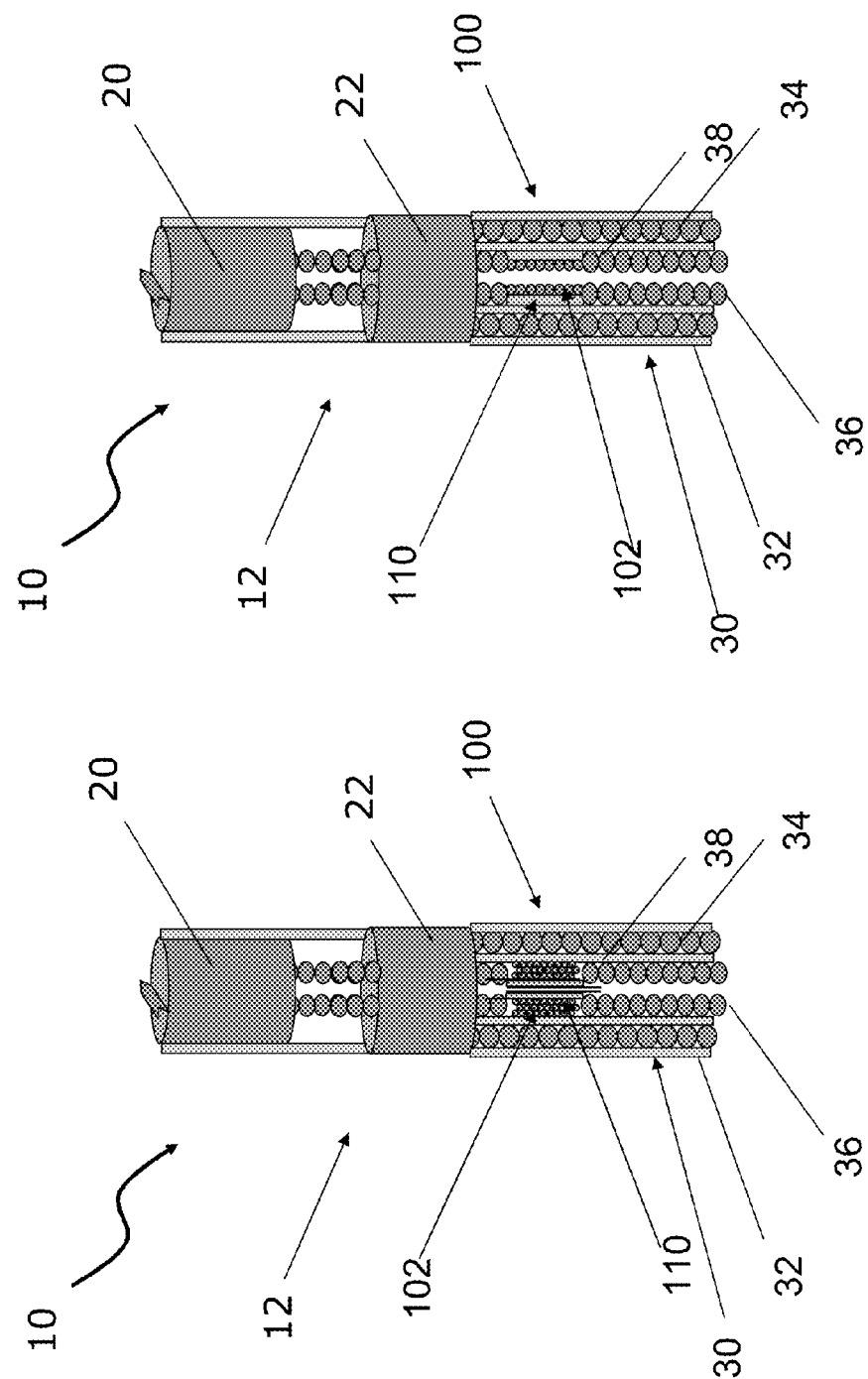

(1)

ELECTRODE DEVICE FOR A MEDICAL IMPLANT, AND A MEDICAL IMPLANT COMPRISING AN ELECTRODE DEVICE

This application claims the benefit of U.S. Provisional Patent Application 61/878,060 filed on 16 Sep. 2013, the specification of which is hereby incorporated herein by reference.

BACKGROUND OF THE INVENTION

1. Field of the Invention

Embodiments of the invention generally relate to an electrode device for a medical implant and to a medical device having an electrode device.

2. Description of the Related Art

Medical implants, such as implantable defibrillators, cardiac pacemakers, etc., stimulate heart muscle with the aid of electrical pulses, which are guided from a battery-operated unit via an electrode to the heart.

Individuals fitted with a cardiac pacemaker, under the action of strong static and alternating magnetic fields of more than one tesla, as are used for example in diagnostic devices such as magnetic resonance tomographs, are typically subject to severe limitations in order to avoid endangerment caused by interaction between the magnetic fields and components of the cardiac pacemaker. Cardiac pacemakers and implantable defibrillators, etc. can be damaged by the strong magnetic fields or may injure the patient as a result of interactions with the magnetic fields. Contact areas of implanted electrodes may heat up, magnetic parts of the implant could move in the magnetic field, or an interference with the function of the electric control of the implant may occur. Those individuals fitted with a cardiac pacemaker should therefore only be subject to examination in a magnetic resonance tomograph under specific conditions, if at all.

In magnetic resonance tomographs, by superimposing a static magnetic field $B_0$ with a magnetic alternating field, a precession movement of a nuclear spin of water molecules is excited in the body of the patient. The precession movement occurring with Larmor frequency. The Larmor frequency is dependent on the strength of the static magnetic field $B_0$ and on the particles in question, for example protons, and is 42.58 MHz for protons at one tesla. The high-frequency additional field, which is oriented transverse to the static magnetic field and of which the frequency is in resonance with the Larmor frequency, deflects all nuclei in a phase-synchronous manner from their current position to the static field $B_o$. Signals upon relaxation of the nuclei, or of the nuclear spin, can be detected and used for highly accurate imaging of the tissue. The Larmor frequency lies in the VHF range and interferes with the electronic components of medical implants.

BRIEF SUMMARY OF THE INVENTION

One object of at least one embodiment of the invention is to provide an electrode device for a medical implant with improved tolerance in terms of the effects of strong magnetic fields.

A further object of at least one embodiment of the invention is to provide a medical implant having a corresponding electrode device.

The objects are achieved in accordance with the invention by the features of the claims. Favorable embodiments and advantages of the invention will emerge from the other claims and the description.

(2)

At least one embodiment of the invention is based on an electrode device for a medical implant, wherein the electrode device has a distal end and a proximal end, between which an electric transmission line extends.

In one or more embodiments, the electric transmission line may include at least one adaptive element. In at least one embodiment, the at least one adaptive element may include a magnetodielectric material with electric and magnetic properties, wherein the magnetodielectric material changes its electric and/or magnetic properties under the action of a magnetic field.

In at least one embodiment, a unit is arranged at the proximal end, in which energy for generating the pulses for stimulating the heart is provided. In one or more embodiments, the distal end is arranged in the vicinity of the heart or directly on the heart.

In at least one embodiment, electronics of the medical implant may advantageously be adapted to the Larmor frequencies of various magnetic resonance devices produced by a respective static magnetic field ($B_0$ field).

Magnetodielectric materials are what are known as multiferroics and have a relative permittivity ($\in_r$) and a magnetic permeability ($\mu_r$) above one. A characteristic feature of these materials is that, when a magnetic field is applied, the relative permittivity $\in_r$ changes, whereas, when an electric field is applied, the magnetic properties ($\mu_r$) change. Representatives of such magnetodielectric materials include, for example, one or more of $BaMnF_4$, $BiMnO_3$, $LiCoPO_4$, $CoCr_2O_4$, $ZnMn_2O_4$, $La_2NiMnO_6$, $GeCo_2O_4$, $Mn_3O_4$, $(Tb, Dy, Ho)Mn_2O_5$, and $(La_{2/3}Ca_{1/3})MnO_3$.

In one or more embodiments, compounds such as $La_2NiMnO_6$ and $(La_{2/3}Ca_{1/3})MnO_3$ have a large effect at ambient temperatures in the case of magnetic fields of around 1 tesla.

A condition for successful application according to at least one embodiment occurs when the relative permittivity $\in_r$ at the transition from 1.5 tesla to 3 tesla changes to ¼ of the relative permittivity $\in_r$, since the following is true: f=1/sqrt(LC), wherein the frequency f thus changes quadratically.

In one or more embodiments, the at least one adaptive element may be arranged at the distal end or in the region of the distal end of the electric transmission line.

In at least one embodiment, the at least one adaptive element may include an electric coil. Magnetodielectric material, in one or more embodiments, may be wound around the coil at least in regions of the electric coil. Alternatively or additionally in at least one embodiment, the coil may surround the magnetodielectric material at least in regions. As such, by way of one or more embodiments, the electric resonance length of the electric coil may thus change in a defined manner depending on an effective magnetic field, in particular a static magnetic field, $B_0$. In at least one embodiment, the coil is thus a controllable coil, wherein the electric properties may change in a known manner dependent on the static magnetic field $B_0$.

In one or more embodiments, a capacitance of the electrode device, depending on the magnetic field, may be represented as:

$$C=1/\sqrt{B_0 \gamma L};$$

wherein $B_0$ is the magnetic flux density, L is the inductance of the component, and $\gamma$ is the gyromagnetic ratio.

In at least one embodiment of the invention, the at least one adaptive element may include an electric capacitor with an electrical capacitance. Under the action of a magnetic field, in one or more embodiments, a value of the electrical capacitance may change in a defined manner dependent on an effective magnetic field, such as a static magnetic field, $B_0$. By way of at least one embodiment, the capacitor is thus a controllable capacitor, wherein the electric properties of the capacitor may be changed in a known manner by the static magnetic field $B_0$. In one or more embodiments, the capacitance of the electrode device, may be formed as a discrete or separate component.

At least one embodiment of the invention may include a filter with a resonance frequency of $f_{res}=1/\sqrt{CL}$, wherein the resonance frequency may correspond to the Larmor frequency $f_{Lamor}=B_0\gamma$ or may be approximated therewith such that a sufficient damping of coupled-in RF fields is achieved.

In at least one embodiment, the electrode device may include an LC band-stop filter, wherein the at least one adaptive element may be part of or include the LC band-stop filter. In one or more embodiments, the LC band-stop filter may adapt automatically to the effective magnetic field $B_0$.

In accordance with a further aspect of at least one embodiment of the invention, the electrode device may be utilized in combination with a cardiac pacemaker.

In accordance with a further aspect of at least one embodiment of the invention, the electrode device may be utilized in combination with an implantable defibrillator.

In accordance with a further aspect of at least one embodiment the invention, a medical implant may be implanted in a human or animal body that includes the electrode device. In these embodiments, the at least one adaptive element may be provided in an electric transmission line. In one or more embodiments, the at least one adaptive element may be located between a unit at a proximal end of the electric transmission line and an electrode tip at a distal end of the electric transmission line. In one or more embodiments, the medical implant may include a magnetodielectric material, wherein under the action of a magnetic field, the electric and/or magnetic properties of the magnetodielectric material may change.

BRIEF DESCRIPTION OF THE DRAWINGS

The above and other aspects, features and advantages of at least one embodiment of the invention will be more apparent from the following more particular description thereof, presented in conjunction with the following drawings wherein:

FIG. 1 shows a first embodiment of a distal end of an electrode device with a magnetodielectric material arranged in an interior of a coil; according to at least one embodiment of the invention;

FIG. 2 shows a further embodiment of a distal end of an electrode device with a magnetodielectric material surrounding a coil; according to at least one embodiment of the invention.

DETAILED DESCRIPTION OF THE INVENTION

Figure 3:
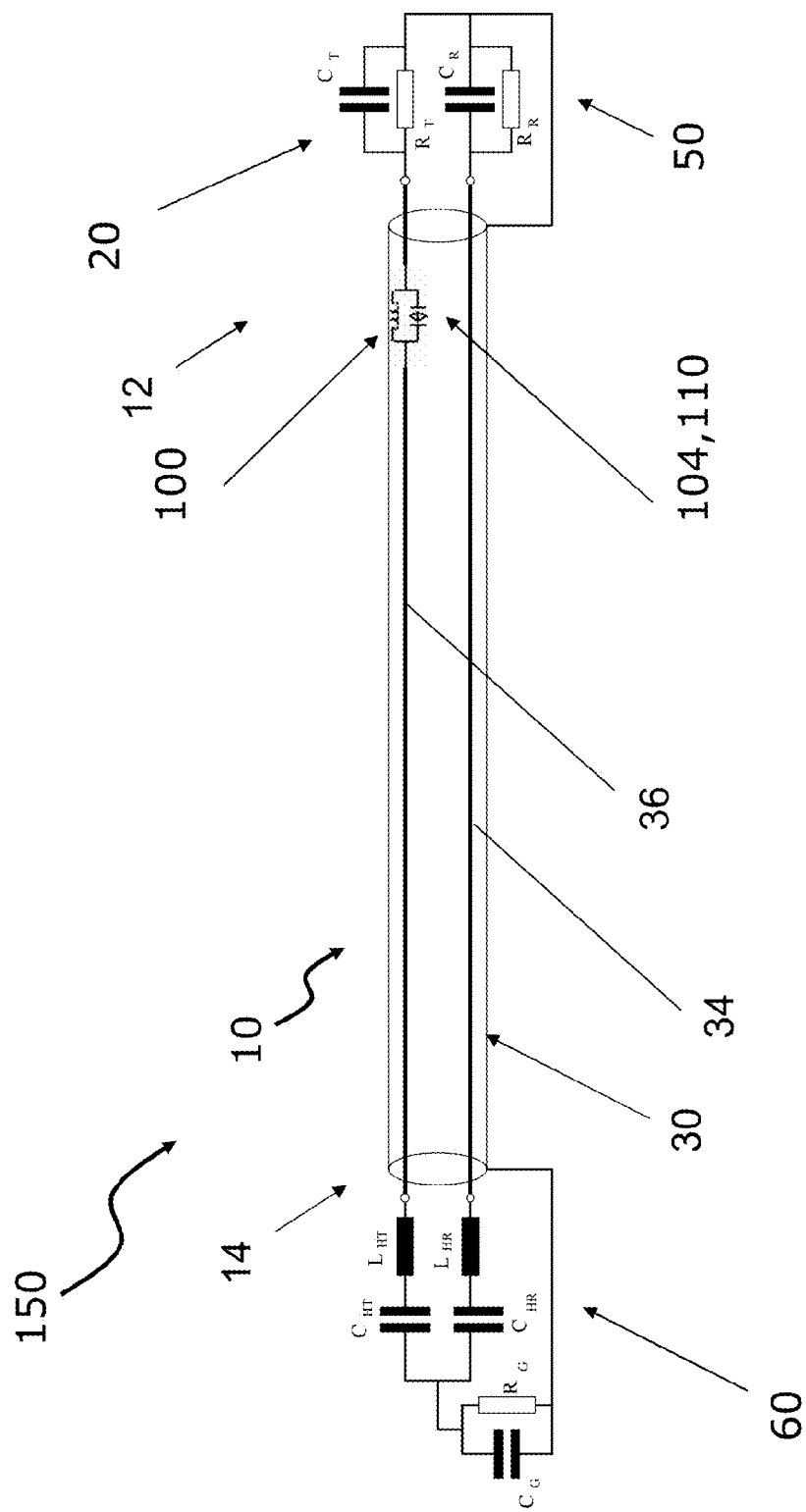
FIG. 3 shows an illustration of a medical implant with an electrode device according to at least one embodiment of the invention.

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

In the figures, functionally like elements or elements acting similarly are denoted by like reference signs in each case. The figures are schematic illustrations of the invention. They do not show specific parameters of the invention. Furthermore, the figures merely reproduce typical embodiments of the invention and are not intended to limit the invention to the embodiments illustrated.

FIG. 1 shows a first embodiment of a distal end of an electrode device with a magnetodielectric material arranged in an interior of a coil, and FIG. 2 shows a further embodiment of a distal end of an electrode device with a magnetodielectric material surrounding a coil, according to at least one embodiment of the invention.

FIGS. 1 and 2, in at least one embodiment of the invention, show an electrode device 10 for a medical implant. In at least one embodiment, the medical implant may include a cardiac pacemaker, an implantable defibrillator, a neurostimulator, a monitoring implant, or the like. In one or more embodiments, the electrode device 10 may include a temporarily implantable or permanently implantable electrode, and may be connected to an external device such as an external cardiac pacemaker, or the like. In at least one embodiment, the electrode device 10 may include a catheter.

As shown in FIGS. 1 and 2, in at least one embodiment of the invention, the electrode device 10 includes a distal end 12 and a proximal end 14 (see FIG. 3). In one or more embodiments, the proximal end may include a unit, such as a control unit, wherein the unit may include a power source, such as a battery, and may include an electronics unit to control and/or regulate electrical pulses. In at least one embodiment, the distal end 12 may include an electrode tip 20, wherein the electrical pulses may be delivered to an area of use, for example to a heart muscle, via the electrode tip 20.

One or more embodiments of the invention may include an electric transmission line 30 with a proximal end and a distal end, wherein the electric transmission line 30 may be located within an electrically insulating sleeve 32. At least one embodiment of the invention may include two concentrically arranged coils 36 (inner coil) and 34 (outer coil) that may extend from one end to the other end of the electrically insulating sleeve 32 and of the electric transmission line 30, and may extend between the proximal end and the distal end 12 of the electrode device 10. One or more embodiments may include an electric insulation 38 that may be located between the inner coil 36 and the outer coil 34. At the distal end 12, by way of at last one embodiment, the outer coil 34 may end at an annular end element 22, through which the inner coil 36 may protrude as far out as the electrode tip 20, and may be in direct contact with the area of use, such as the heart.

One or more embodiments of the invention may include at least one adaptive element 100, which may be located in the electric transmission line 30, and may be located in the region of the distal end 12. In at least one embodiment, the at least one adaptive element 100 may include a magnetodielectric material 110 with electric and magnetic properties, wherein the magnetodielectric material 110 changes its electric and/or magnetic properties under the action of a magnetic field.

According to one or more embodiments, the at least one adaptive element 100 may be located at the proximal end, and protects the electrode device 10, or the implantable device, against high-frequency currents, however heating at the distal end may not be suppressed.

By way of at least one embodiment, as shown in FIGS. 1 and 2, the at least one adaptive element 100 in the electric transmission line 30 may be formed as, or include, an electric coil or coil 102. FIG. 1 shows, according to at least one embodiment, the distal end of the electrode device with the magnetodielectric material 110 that may be arranged in the interior of the coil 102. In one or more embodiments, the coil 102 may be wound around a core made of magnetodielectric material. FIG. 2 shows, according to at least one embodiment of the invention, the distal end 12 of the electrode device 10 with the layer of magnetodielectric material 110 that surrounds the coil 102. At least one embodiment of the invention may include one or more layers of the magnetodielectric material 110, wherein at least one of the magnetodielectric material layers may be wound around the coil 102. In one or more embodiments, the at least one adaptive element 100 interrupts the inner coil 36. If the electric properties of the at least one adaptive element 100 change when a strong external magnetic field $B_0$ is effective, by way of at least one embodiment, the resonance length of the electric transmission line 30, such as the inner coil 36, changes accordingly.

FIG. 3 shows a medical implant 150, such as a cardiac pacemaker or implantable defibrillator, with an electrode device 10.

In at least one embodiment of the invention, the electrode device 10 may include the electric transmission line 30, such as a shielded electric transmission line, with distal end 12 and a proximal end 14. In one or more embodiments, the proximal end 14 may include a control electronics system or control unit 60 that may include one or more of capacitors, coils and electric resistors. The control electronics system 60, in at least one embodiment, may control and/or regulate delivery of electrical pulses from the electrode tip 20. At least one embodiment of the invention may include one or more of a battery and a microprocessor.

In one or more embodiments, the at least one adaptive element 100 may be located at the distal end 12 of the electric transmission line 30, and may include a capacitor, such as an electric capacitor, 104. At least one embodiment of the invention may include an LC band-stop filter, and wherein that at least one adaptive element 100 may be part of the LC band-stop filter. Tip and ring electrodes may be modeled with capacitor $C_T$, resistor $R_T$ and capacitor $C_R$ and resistor $R_R$ respectively. The line 50 illustrated outside of the transmission line 30 represents the electric connection between tip electrode and ring electrode formed by the surrounding tissue and/or fluids. The components $C_T$ and $R_T$ represent the capacitive and resistive coupling of the tip electrode to the surrounding tissue and/or fluids respectively. The components $C_R$ and $R_R$ represent the capacitive and resistive coupling of the ring electrode to the surrounding tissue and/or fluids respectively. The components $C_{HT}$, $L_{HT}$ represent the equivalent circuit of the feed through of the tip connector, namely the equivalent capacitance and inductance. The components $C_{HR}$, $L_{HR}$ represent the equivalent circuit of the feed through of the of the ring connector respectively. The components $C_G$ and $R_G$ represent the equivalent circuit of the coupling of the housing of the medical implant to the surrounding tissue and/or fluid similar to $C_T$, $R_T$, $C_R$ and $R_R$.

According to at least one embodiment of the invention, the electric capacitor 104 may include magnetodielectric material 110, wherein under the action of a magnetic field, the magnetodielectric material 110 may change its electric and/or magnetic properties. In one or more embodiments, the magnetodielectric material may be located between capacitor electrodes poled in opposite directions. In at least one embodiment, the capacitor 104 may be formed as a separate component.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An electrode device for a medical implant comprising:
   a distal end and a proximal end; and,
   an electric transmission line extending between said distal end and said proximal end;
   wherein said electric transmission line comprises a transmission line distal end, a transmission line proximal end and at least one adaptive element,
   wherein the at least one adaptive element comprises a magnetodielectric material with electrical properties comprising a relative permittivity ∈r and magnetic properties comprising a magnetic permeability μr, and,
   wherein under action of a magnetic field, the relative permittivity ∈r of the magnetodielectric material changes, and wherein under action of an electric field, the magnetic permeability μr of the magnetodielectric material changes.

2. The electrode device as claimed in claim 1, wherein the transmission line distal end of the electric transmission line comprises said at least one adaptive element.

3. The electrode device as claimed in claim 1, wherein the at least one adaptive element comprises an electric coil.

4. The electrode device as claimed in claim 3, wherein the magnetodielectric material is wound around the electric coil in one or more regions.

5. The electrode device as claimed in claim 3, wherein the electrical coil surrounds the magnetodielectric material in one or more regions.

6. The electrode device as claimed in claim 4, wherein the electric coil surrounds the magnetodielectric material in one or more regions.

7. The electrode device as claimed in claim 1, wherein the at least one adaptive element comprises an electric capacitor.

8. The electrode device as claimed in claim 1, further comprising an LC band-stop filter, wherein the LC band-stop filter comprises said at least one adaptive element.

9. The electrode device as claimed in claim 1, wherein said electrode device is coupled with a cardiac pacemaker.

10. The electrode device as claimed in claim 1, wherein said electrode device is coupled with a defibrillator.

11. The electrode device as claimed in claim 1, wherein the electrode device is configured to be implanted in a human or animal body, wherein the at least one adaptive element is located between the transmission line distal end and the transmission line proximal end.

12. The electrode device as claimed in claim 1, wherein the electric transmission line further comprises an electric coil, and wherein the magnetodielectric material is in an interior of the electric coil.

13. The electrode device as claimed in claim 1, wherein when the electrical properties of the magnetodielectric material change under the action of the magnetic field, a resonance length of the electric transmission line changes accordingly.

14. The electrode device as claimed in claim 1, wherein when the electrical properties of the magnetodielectric material change under the action of the magnetic field, a resonance length of the electric transmission line changes accordingly and wherein the relative permittivity ∈r at 3 tesla changes to ¼ of the relative permittivity ∈r at 1.5 tesla.

15. An electrode device for a medical implant comprising:
a distal end and a proximal end; and,
an electric transmission line extending between said distal end and said proximal end;
wherein said electric transmission line comprises a transmission line distal end, a transmission line proximal end and at least one adaptive element,
wherein the at least one adaptive element comprises a magnetodielectric material with electrical properties and magnetic properties,
wherein the magnetodielectric material changes one or more of the electrical properties and the magnetic properties under action of a magnetic field; and,
wherein the electric transmission line further comprises an electric coil, and wherein the magnetodielectric material is in an interior of the electric coil.

16. An electrode device for a medical implant comprising:
a distal end and a proximal end; and,
an electric transmission line extending between said distal end and said proximal end;
wherein said electric transmission line comprises a transmission line distal end, a transmission line proximal end and at least one adaptive element,
wherein the at least one adaptive element comprises a magnetodielectric material with electrical properties and magnetic properties,
wherein the magnetodielectric material changes one or more of the electrical properties and the magnetic properties under action of a magnetic field; and,
wherein when the electrical properties of the magnetodielectric material change under the action of the magnetic field, a resonance length of the electric transmission line changes accordingly.

* * * * *